United States Patent [19]

Beaucamp et al.

[11] 4,360,596

[45] Nov. 23, 1982

[54] PROCESS FOR THE PREPARATION OF CHOLESTEROL ESTERASE

[75] Inventors: Klaus Beaucamp; Michael Nelboeck; Helmgard Gauhl; Hans Seidel, all of Tutzing; Wolfgang Gruber, Tutzing-Unterzeismering; Herwig Brunner, Weilheim, all of Fed. Rep. of Germany

[73] Assignee: Boehringer Mannheim GmbH, Mannheim, Fed. Rep. of Germany

[21] Appl. No.: 175,809

[22] Filed: Aug. 6, 1980

[30] Foreign Application Priority Data

Aug. 20, 1979 [DE] Fed. Rep. of Germany ....... 2933648

[51] Int. Cl.³ ............................................. C12N 9/18
[52] U.S. Cl. .................................... 435/197; 435/874

[58] Field of Search .................... 435/197, 196, 11

[56] References Cited

U.S. PATENT DOCUMENTS 3,925,164 12/1975 Beaucamp et al. ............. 435/197 X
4,011,138  3/1977 Terada et al. ........................ 435/197
4,052,263 10/1977 Masurekar et al. ................ 435/197

*Primary Examiner*—Lionel M. Shapiro
*Attorney, Agent, or Firm*—Felfe & Lynch

[57] ABSTRACT

The present invention provides a process for obtaining cholesterol esterase from micro-organisms of the genus Pseudomonas, wherein Pseudomonas sp. DSM 1280 or DSM 1281 is cultured in an appropriate culture medium in the presence of an inducer and the enzyme is obtained from the culture medium and/or from the cells.

5 Claims, No Drawings

PROCESS FOR THE PREPARATION OF CHOLESTEROL ESTERASE

The present invention is concerned with a process for obtaining cholesterol esterase from micro-organisms.

Cholesterol esterase has played an important role in clinical and biochemical analysis ever since processes have been developed for the enzymatic determination of cholesterol. Since a large part of the cholesterol in biological material is present in the form of esters, the joint use of cholesterol esterase and cholesterol-oxidizing enzymes, such as cholesterol oxidase or cholesterol dehydrogenase, makes possible a completely enzymatic determination of cholesterol esters. This is known from Federal Republic of Germany Patent Specification No. 2,264,847. The enzyme from micro-organisms has proved to be especially suitable for determination processes involving the use of cholesterol esterase (see Federal Republic of Germany Patent Specification No. 2,506,712). However, a disadvantage of the previously discovered micro-organisms with a content of cholesterol esterase which is sufficiently great to make a working up thereof worthwhile is the relatively low yields of enzyme activity which are obtained.

Surprisingly, we have now found that when using certain micro-organisms, several times higher activities can be achieved than was previously possible.

Thus, according to the present invention, there is provided a process for obtaining cholesterol esterase from micro-organisms of the genus Pseudomonas, wherein Pseudomonas sp. DSM 1280 or DSM 1281 is cultured in an appropriate nutrient medium in the presence of an inducer and the enzyme is obtained from the culture medium and/or from the cells.

From Federal Republic of Germany Patent Specification No. 2,527,068, species of the genus Pseudomonas, namely *Pseudomonas fluorescens*, are admittedly already known which also have a content of cholesterol esterase which is sufficient to make a working up thereof an economic proposition. However, in this case, too, the units of activity obtainable are low and, in many cases, amount to only a few units per liter. In contradistinction thereto, with the micro-organisms used according to the present invention, activities of 15,000 units and more per liter can be achieved.

According to the process of the present invention, culturing is carried out in a nutrient medium which contains an inducer. By "inducer", there is to be understood a substance which stimulates the microorganisms to form the desired enzyme in larger amounts than without the use of an inducer. The inducer is also used as a source of carbon and especially as the sole source of carbon. However, it is also possible to add separate sources of carbon, for example maize steep liquor, peptones and yeast extracts, as well as, but less preferably, sugars and polyalcohols, such as glycerol. Palmitic esters and especially tripalmitin, have proved to be good inducers. However, the best results have been achieved with the use of lecithin as inducer. Amongst the various lecithins, soya lecithin has proved to be especially suitable but also other types of lecithin, such as egg lecithin and brain lecithin, have also given very good results.

The amount of inducer added is, to a certain extent, dependent upon the nature of the inducer used. In general, it is from about 0.1 to 5% by weight, referred to the volume of the nutrient medium. In the case of using lecithin as inducer and as the sole source of carbon, especially good results have been obtained with an amount of from 0.5 to 2% by weight.

Furthermore, the nutrient medium also contains the conventionally added salts and trace elements and, by the addition of appropriate buffers, should be adjusted to a pH value of from about 5 to 9 and preferably of from 6 to 8. The buffer used is preferably a phosphate buffer. Furthermore, the nutrient medium preferably also contains ammonium, chlorine, iron, copper, zinc, magnesium and calcium ions, apart from the alkali metal ions of the phosphate buffer. The phosphate is preferably present in a concentration of from 0.4 to 2% by weight can also be added in higher or lower concentrations.

Animal fats and, surprisingly, also cholesterol esters prove to be less advantageous as inducers in the process according to the present invention.

A nutrient medium which is preferred according to the present invention has approximately the following composition, referred to 1 liter of liquid:

5 to 10 g. and preferably 6 to 8 g. disodium monohydrogen phosphate dihydrate,
1 to 5 g. and preferably 2 to 4 g. monopotassium dihydrogen phosphate,
0.2 and 2 g. and preferably 0.8 to 1.2 g. ammonium chloride,
0.01 to 0.1 g. and preferably 0.3 to 0.7 g. sodium chloride,
0.01 to 1 ml. 1% ferric chloride solution,
0.01 to 1 ml. 0.2% cupric chloride solution,
0.01 to 1 ml. 1% zinc sulphate solution,
0.1 to 10 ml. 10% calcium chloride solution,
1 to 20 ml. and preferably 3 to 10 ml. 12% magnesium sulphate solution, and
0.1 to 5% by weight and preferably 0.5 to 2% by weight soya lecithin.

Culturing is carried out under aerobic conditions. There can be used not only a shake culture but also an aerated submersion culture. The temperature can be from about 15° to about 45° C. but is preferably from 25° to 35° C. Generally speaking, maximum enzyme yields are obtained after a culture period of only 1 to 2 days.

The micro-organisms employed according to the present invention are very similar and exhibit the following characteristics:

Gram negative,
obligatory aerobic,
yellowish colonies on meat peptone agar,
growth at 25°, 30° and 37° C.,
no growth at 10° C. and at more than 41° C.,
cell size 0.8 to 1μ×2 to 4μ,
motile, lophotrichously covered,
tendency to chain formation,
no spores or permanent stages,
cytochrome oxidase reaction: +
catalase reaction: (+)
indole reaction: −
nitrite reaction: −
Voges-Proskauer reaction:
gelatine reaction: −

The also break down the following substrates: adonite, citrate, galactose, glucose, inositol, lactose, mannitol, mannose, salicin and sorbitol.

The cholesterol esterase occurs not only in the culture medium but also in the cells. By means of the addition of surface-active agents, especially of nonionic agents, which are preferably of the polyoxyethylene ester and ether types with alkyl and aralkyl radicals, the partition pattern between the culture broth and the cells can be influenced in the sense of increasing the extracellular activity at the expense of the intracellular activity, whereas when using ionic surface-active agents, a change in the partitioning takes place in the opposite direction.

When culturing is finished, the cholesterol esterase is isolated from the cell mass and/or from the culture filtrate in the usual manner and, if desired, is purified. However, for many purposes, use can be made of an impure crude product which consists essentially only of a digested cell mass. For digestion, use can be made of the methods known for this purpose, which do not need to be explained here. The enzyme can be precipitated not only from the culture filtrate but also from the digested cell mass, after separation of insoluble components, by precipitation with conventional precipitation agents, for example salts, such as ammonium sulphate, or organic solvents, such as acetone or alcohols, and then further purified by conventional fractionation methods, such as chromatography and precipitation.

The following Examples are given for the purpose of illustrating the present invention:

EXAMPLE 1

Psuedomonas spec. DSM 1280, taken from a deep cooled ampoule on tilted tubelets, is aerobically (shaking flask) pre-cultured in the main culture medium for 2 days at 30° C. and then inoculated in an amount of 10% into a medium which, per liter, has the following composition:

7 g. disodium monohydrogen phosphate dihydrate,
3 g. monopotassium dihydrogen phosphate,
1 g. ammonium chloride,
0.05 g. sodium chloride,
0.1 ml. 1% ferric chloride solution,
0.1 ml. 0.2% cupric chloride solution,
0.1 ml 1% zinc sulphate solution,
1.0 ml. 10% calcium chloride solution,
5.0 ml. 12% magnesium sulphate solution,
1.5% soya lecithin,
pH 7.0.

Culturing is carried out aerobically at 30° C. in a shake flask. After 1 to 3 days, activities of about 15,000 U/liter are obtained (supernatant and biomass; substrate: cholesteryl oleate).

About the same yields are obtained when, under the same conditions, instead of Pseudomonas spec. DSM 1280, there is used Pseudomonas spec. DSM 1281.

EXAMPLE 2

The insoluble cell mass is centrifuged off from a culture solution obtained according to Example 1 and used for the determination of cholesterol esters. The determination is carried out according to the following reaction equations:

(1) cholesterol ester + H$_2$O 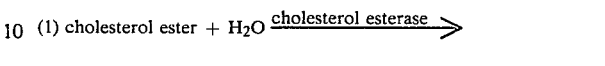

cholesterol + fatty acid (2) cholesterol + ½ O$_2$ 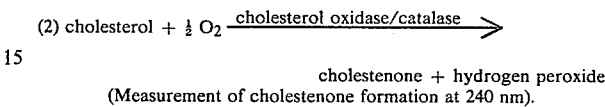

cholestenone + hydrogen peroxide
(Measurement of cholestenone formation at 240 nm).

The following solutions are used for the measurement:

(1) phosphate buffer, 0.5 M, pH 7.5; 0.4% thesit
(2) cholesterol oleate, c=4 in thesit/dioxan (1:1 v/v)
(3) hydrogen peroxide about 0.6 M (5 ml. perhydrol/100 ml.)
(4) catalase (0.01 mg. protein/ml.)
(5) cholesterol oxidase (at least 50 U/ml.)
(6) culture solution (in the case of about 5000 U/liter, dilute 1:5 with water, 0.01 ml. per test).

For carrying out the measurement, 2.95 ml. of Solution (1) are mixed with 0.02 ml. of Solution (3). After 5 minutes, 0.01 ml. of Solution (6) and 0.02 ml. of Solution (5) are added thereto and, after 1 minute, the reaction is started by the addition of 0.1 ml. of Solution (2).

The calculation is carried out as follows:

$$\frac{3.12 \times 5 \times 1000}{15.5 \times 0.01} \times \Delta E/\text{min.} = U/l. \text{ culture solution.}$$

It will be understood that the specification and examples are illustrative but not limitative of the present invention and that other embodiments within the spirit and scope of the invention will suggest themselves to those skilled in the art.

What is claimed is:

1. Process for obtaining cholesterol esterase from micro-organisms, which process comprises culturing Psuedomonas sp. DSM 1280 or DSM 1281 in a culture medium in the presence of an inducer, and recovering the enzyme obtained from the culture medium or the cells.

2. Process as claimed in claim 1 wherein culturing is carried out in the presence of about 0.1 to 5% by weight of inducer.

3. Process as claimed in claim 1 wherein 0.4 to 2% by weight of phosphate is added to the culture medium.

4. Process as claimed in claim 1 wherein the microorganisms Psuedomonas sp. is DSM 1280.

5. Process as claimed in claim 1 wherein the microorganism Pseudomonas sp. is DSM 1281.

* * * * *